(12) United States Patent
Zhu et al.

(10) Patent No.: US 10,665,327 B2
(45) Date of Patent: May 26, 2020

(54) HIGH-THROUGHPUT HYBRIDIZATION AND READING METHOD FOR BIOCHIPS AND SYSTEM THEREOF

(71) Applicants: Zhiyuan Zhu, Plainsboro, NJ (US); Libo Chen, Plainsboro, NJ (US)

(72) Inventors: Zhiyuan Zhu, Plainsboro, NJ (US); Libo Chen, Plainsboro, NJ (US)

(*) Notice: Subject to any disclaimer, the term of this patent is extended or adjusted under 35 U.S.C. 154(b) by 0 days.

(21) Appl. No.: 16/288,895

(22) Filed: Feb. 28, 2019

(65) Prior Publication Data

US 2020/0105369 A1 Apr. 2, 2020

Related U.S. Application Data

(63) Continuation of application No. 16/182,508, filed on Nov. 6, 2018.

(60) Provisional application No. 62/739,321, filed on Sep. 30, 2018.

(51) Int. Cl.
| | | |
|---|---|---|
| *G01N 33/48* | (2006.01) | |
| *G16B 25/30* | (2019.01) | |
| *C12Q 1/6837* | (2018.01) | |
| *B01J 19/00* | (2006.01) | |
| *G16B 25/20* | (2019.01) | |

(52) U.S. Cl.
CPC .......... *G16B 25/30* (2019.02); *B01J 19/0046* (2013.01); *C12Q 1/6837* (2013.01); *G16B 25/20* (2019.02); *B01J 2219/00587* (2013.01); *B01J 2219/00608* (2013.01); *B01J 2219/00722* (2013.01)

(58) Field of Classification Search
None
See application file for complete search history.

(56) References Cited

FOREIGN PATENT DOCUMENTS

CN 101034061 A 9/2007

OTHER PUBLICATIONS

"U.S. Appl. No. 16/182,508, Preliminary Amendment filed Feb. 14, 2019", 4 pgs.
"U.S. Appl. No. 16/182,508, Supplemental Preliminary Amendment filed Apr. 30, 2019", 6 pgs.

*Primary Examiner* — Anna Skibinsky
(74) *Attorney, Agent, or Firm* — Schwegman Lundberg & Woessner, P.A.

(57) ABSTRACT

A high-throughput hybridization and reading method for biochips uses probes with different marks to specifically connect single nucleotide loci by conducting connection between the probes and target genes at different temperatures, and performing hybridization at the same temperature after the probes are connected, thereby achieving hybridization detection for various loci in a single chip. The method enables fast detection for multiple loci as required by personalized medicine. The detection is high-throughput and systematized and provides highly visualized and highly accurate results. The method allows detection for different loci at different hybridization temperatures to be done simultaneously. The method features highly uniform and repeatable detection, making biochips more efficient and utility in terms of detection. Besides, the chip is easy to prepare and use, thus having a good promotional value.

10 Claims, 2 Drawing Sheets

Specification includes a Sequence Listing.

HIGH-THROUGHPUT HYBRIDIZATION AND READING METHOD FOR BIOCHIPS AND SYSTEM THEREOF

CROSS REFERENCE TO RELATED APPLICATIONS

This application is a continuation of U.S. patent application Ser. No. 16/182,508, filed Nov. 6, 2018, which claims priority to U.S. provisional application No. 62/739,321 filed Sep. 30, 2018, both of which are incorporated herein.

BACKGROUND OF THE INVENTION

1. Technical Field

The present invention relates to biochip-based assays, and more particularly to a high-throughput hybridization and reading method for biochips and its system.

2. Description of the Related Art

I. Biochips and Gene Chips

A biochip or a bioarray is based on the principle of specific interactions between biomolecules, and integrates the biochemical analysis process in its chip surface, so as to facilitate rapid and high-throughput detection of DNA, RNA, polypeptides, proteins and other biological components. In a narrow sense, a biochip is a biomolecule lattice made by adhering biomolecules (e.g. oligonucleotides, cDNA, genomic DNA, polypeptides, antibodies, antigens, etc.) to a solid-phase transmitter, such as a silicon wafer, a glass sheet (bead), a plastic sheet (bead), gel, a nylon film in various ways. As a part of the gene industry, biochips have great application prospect.

The major features of biochips are high throughput, miniaturization and automatization. With tens of thousands of closely arranged molecules integrated as a microarray, a biochip is capable of analyzing numerous biomolecules in a short period of time and providing people with accurate biological information about their samples at a detection efficiency up to a thousand times of that of the traditional approaches. In the biochip technology, gene chips have been the first commercialized products and are currently the most mature. Gene chips are developed based on the principle of nucleic-acid-probe complementary hybridization technology. The so-called nucleic-acid-probe is just an artificially composed base sequence. The probe is connected to certain detectable substance. According to the principle of base complementarity, the gene probe can be used to identify specific genes in a gene mixture.

On the other hand, a gene chip is also known as a DNA chip or a DNA microarray. It is quite similar to chips used in computers, with the only difference that it has tens of thousands of gene probes densely integrated therein as a grid. It uses a DNA fragment having a known base sequence to bond with a single-stranded DNA having a base complementary sequence, so as to determine the corresponding sequence, thereby identifying abnormal genes or their products. Currently, gene chips for detection of gene mutation and gene expression spectrum chip for detection of gene expression levels are relatively mature products. The gene chip technology principally comprises four fundamental technical parts: preparation of chip microarrays, preparation of samples, biomolecule reaction, as well as detection and analysis of signals.

II. Biochips for SNP detection

In 2001, the SNP Consortium developed variation human genetic map containing $1.42 \times 10^6$ SNPs, with a density of one single-nucleotide polymorphism locus in every 1.9 kb-fragment. This is every important to researches on virulence genes and the origin and evolution of mankind. As estimated, there will be about one hundred thousand SNP molecular markers used for researches on gene functions and diseases. Such huge analysis needs demand highly for detection technologies.

At present, there are several common methods for detection of single-nucleotide polymorphism of alleles.

The first is allele-specific amplification. It is to make the 3'-end of the designed Primer 1 complementary to the sequence of a to-be-detected P allele in a polymerase chain-reaction system, and not complementary to the sequence of another allele (Q). During the PCR amplification, the P allele amplified. In the same manner, the designed Primer 2 is complementary to the sequence of Q, and then the amplified products are analyzed through electrophoresis respectively. While this known method can detect single-nucleotide polymorphism, its operation is complicated and it has higher requirements about primer design, resulting in difficult operation and huge workload.

The second is bidirectional PCR amplification of specific alleles (bi-PASA), which is based on the same principle as allele-specific amplification except that bi-PASA uses 4 primers, wherein Primer F1 has its sequence complementary to that of the 5'-end in a to-be-detected X allele; Primer R2 has its sequence complementary to that of the 3'-end in a to-be-detected Y allele; Primer R1 is located middle-to-downstream in the sequence of X, with its 3'-end being X; and Primer F2 is located middle-to-upstream in the sequence of Y, with its 3'-end being Y. Therein, X and Y each represents a polymorphic locus. During PCR amplification, two oligonucleotide sequences containing single-nucleotide polymorphism loci can be obtained simultaneously. This allows a target gene to be identified in a single round of polymerase chain reaction. While this known approach is operationally simple and economic, it is conducted in the liquid phase and there is only a limited number of multiple parallel reactions, thus failing to provide high-throughput detection for single-nucleotide polymorphism.

The third is primer extension, which identifies base polymorphism loci using DNA polymerase, and provides better specificity as compared to those methods based on allele-specific hybridization. This kind of methods have many names, such as minisequencing, single-nucleotide primer extension (SnuPE), primer-guided nucleotide incorporation, and template directed dye terminator incorporation (TDI). Therein, minisequencing is the most popular. The process involves obtaining a fragment of DNA containing single-nucleotide polymorphism loci first through amplification, and then performing minisequencing, in which a detection primer is introduced, its 3'-end base is immediately next to the polymorphism base, and extension of a base is conducted with the presence of DNA polymerase and marked ddNTPs. The extended base is a polymorphism base. Since the primer for the polymerase chain reaction competes with the extension primer, plural amplified fragments are generated, the surplus dNTPs lead to extension of plural bases in the extension reaction. Thus, before minisequencing, the polymerase chain reaction products have to be purified in order to remove the polymerase chain reaction primers and dNTPs contained therein. The primer extension products may be detected using radioisotope labeling, luminescence detection, gel-based fluorescence detection, mass spectrometry, and denaturing high performance liquid chromatography. However, these methods more or less have disadvantages and shortcomings about high costs and complicated operation. For example, while radioisotope labeling and luminescence are highly automated and convenient, they require high equipment costs. On the other hand, gel-based fluorescence detection is relatively economic yet requires complicated and effort-consuming preparation.

Analysis of single-nucleotide polymorphism based on allele-specific oligonucleotide (ASO) hybridization is the simplest hybridization-based detection method. During hybridization of a short nucleic-acid probe and a complementary target fragment, the hybridization complex will have different levels of stability for a perfect match case and a mismatch case, and single-nucleotide polymorphism loci can be detected based on this difference. This method first involves designing a short nucleic-acid probe, normally 15-20 bp. The probe contains single-nucleotide polymorphism loci. When it is hybridized with a sample DNA, a one-base difference in the 20 bp results in a Tm value decrease of 5-7.5 degrees. Thus, by strictly controlling the conditions for hybridization, it is possible to determine whether there is single-nucleotide polymorphism in the sample DNA. However, the defects of this method lie on not only the difficulty in stringently controlling hybridization, but also incapability of distinguishing single-nucleotide polymorphism loci more accurately.

To realize more stringent hybridization and to better distinguish single-nucleotide polymorphism loci, a modified nucleic acid probe is used for hybridization with the sample DNA, such as a peptide nucleic acid (PNA) probe. Nevertheless, a probe made of peptide nucleic acid is less soluble, thus being unfavorable to reaction. Besides, the probe shall be at least as long as 7 bases, so as to ensure good hybridization at room temperature. For a probe rich in guanine rhodamine markers, its high background fluorescence polarization (FP) signals also pose problems. Another reported solution is to artificially insert a mismatch base (3'-nitropyrrole) into a probe. By using such a probe containing mismatch bases for hybridization, the one-base difference between the probe and a target fragment can decrease the Tm value twice as many as using the traditional hybridization, making hybridization more specific. However, this known method requires strict control on hybridization conditions, and its detection is not accurate enough.

TagMan is a method for in vitro gene amplification based on the principle of hybridization and conventional polymerase chain reaction. The existing method involves adding probes designed for single-nucleotide polymorphism loci and flanking sequences into a polymerase chain reaction system. There is only a one-base difference between different probes, corresponding to different alleles, respectively. In addition, the probes are marked with fluorescence and are terminally phosphorylated to prevent the probe from being extended during amplification. The probes can specifically bond with the target sequence. When the probe is intact, due to the quenching group, the fluorescent marker is prevented from fluorescence through fluorescence resonance energy transfer (FRET). During amplification in polymerase chain reaction, with the activity of the exonucleases of the TagMan DNA polymerase 5'-3'-end, the fluorescent marker at the 5'-end of the probe can be cut off from the probe, thereby allowing fluorescence signal to be released. Since the process happens during polymerase chain reaction, neither isolation nor elution is required, thereby reducing the risk of PCR contamination. Besides, analysis of the amplified products is convenient, fast, and accurate, without using electrophoresis, so the experiment can be done more rapidly. However, since the designed probes have only one-base differences, the requirement is very strict. Moreover, the detection result is merely useful in determination of genotype of one SNP locus, making the detection throughput limited and failing to meet the current demand of high-throughput detection.

CN 101034061 discloses a method for detecting single-nucleotide polymorphism with biochips, which involves performing amplification on a nucleic acid sample first to obtain an amplified product; then performing liquid phase hybridization and ligase reaction to connect the perfect match probe in solution hybridization with the universal probe, thereby detecting single nucleotide polymorphism; and performing solid-phase hybridization to hybridize the probe having label probes at its 5'-end and detection groups at its 3'-end with the biochip at 25° C.-75° C. for 0.5 h-36 h, so that the detection groups are distributed to different sites in the biochip; and performing single-nucleotide polymorphism detection to get results. However, the patented method does not teach how to make detection of multiple single-nucleotide polymorphism loci in a high-throughput manner.

The prior art also has the following shortcomings:
1. The detection adds workload and is time-consuming. The conventional single-nucleotide polymorphism detection methods such as normal polymerase chain reaction and fluorescence quantitative polymerase chain reaction can only detect one or a few single-nucleotide polymorphism locus at a time, and are incapable of simultaneous detection for numerous single-nucleotide polymorphism loci;
2. The probes provided in the traditional biochips are all species-specific, so each chip is only useful in detection of a single particular species. For change or for addition of the detection objects, the only way is to make a new chip. Thus, the prior art is inefficient and not suitable for simultaneous detection of multiple samples and detection of plural loci in a single sample.

SUMMARY OF THE INVENTION

In view of the shortcomings of the prior art, the present invention provides a high-throughput hybridization and reading method for biochips, which simultaneously detects plural SNP loci in a single chip. For detection of each SNP locus, the method comprising the following steps:
a) performing PCR amplification on a double-stranded DNA to be detected, and marking one of its strands with a marker;
b) separating the amplified double-stranded DNA, keeping the DNA strand labeled with the marker, and naming it as a to-be-detected DNA strand;
c) introducing the to-be-detected DNA strand, a first probe, a second probe, and a third probe into one reaction system for polymerase chain reaction, wherein, the 3'-end through 5'-end of the first probe are a first hybridization region and a first complementary region, respectively, and the 5'-end is an A base or a G base; the 3'-end through 5'-end of the second probe are a second hybridization region and a second complementary region, respectively, and the 5'-end is a C base or a T base; the 5'-end of the third probe is attached to fluorescent groups or chromophoric groups; and neither of the first and the second hybridization regions is complementary to the to-be-detected DNA,
both of the first and the second complementarity regions are complementary to the to-be-detected DNA strand, the 5'-end of the second probe or the first probe is complementary to an SNP locus of the to-be-detected DNA, the first probe and the second probe have at least 10 same bases from their 5'-ends to the 3'-ends and have different intervals, which comprise at least 50% of all bases of each probe; and d) when the polymerase chain reaction ends, transferring the reaction liquid to the biochip, which has been fixed with fragments complementary to the first hybridization region of the first probe and the second hybridization region of the second probe, respectively, thereby accomplishing hybridization of the single SNP locus;

For detection of multiple SNP loci, depending on SNP loci of the be-detected DNA, designing a first, a second, and a third probe sequences, and repeating Step a) through Step d); so as to obtain a chip or chips having the plural SNP loci; performing specific reaction with the resulting chip(s) to obtain precipitation or fluorescence, and determining types of the SNP loci according to results of the specific reaction.

According to a preferred mode, the marker in Step a) includes but is not limited to: a biotin, an avidin, and a streptavidin.

According to a preferred mode, the fluorescent group of the third probe in Step c) includes but is not limited to: FAM, HEX, TET, JOE, TAMRA, Texas Red, ROX, CY3 and CY5.

According to a preferred mode, the chromophoric group of the third probe in Step c) includes but is not limited to: ECL, NBT/BCIP and DAB.

According to a preferred mode, the number of the bases in each of the first and second hybridization regions is 15 to 25.

According to a preferred mode, the number of the bases in each of the first and second complementarity regions is 15 to 25.

According to a preferred mode, detection channels for the fluorescent groups are: FAM; 465 to 510 nm; CY3: 533 to 580 nm; HEX: 533 to 580 nm; TET: 533 to 580 nm; JOE: 533 to 580 nm; Texas Red: 533 to 610 nm; ROX: 533 to 610 nm; CY5: 618 to 660 nm; and TAMRA: 533 to 580 nm.

According to a preferred mode, Tm values corresponding to the probes are independently greater than 25° C.

According to a preferred mode, PCR amplification system is a 25 µL reaction system, which comprises: 10×PCR buffer solution 2 µL, 25 mM MgCl 1.5 µL, 0.2 mM×dNTPs 0.5 µL, 5 U/µL Taq DNA polymerase 0.25 µL, 100 µM forward primer 0.1 µL, 100 µM reverse primer 0.1 µL, ddH20 making up to 25 µL According to a preferred mode, the reaction condition for the PCR polymerase chain reaction is: 95° C. initial denaturation 5 min; 95° C. 2 s; 58° C. 10 s; 60° C. 1 min, 40 cycles in total.

The present invention further provides a high-throughput hybridization and reading system for biochips. The system uses the disclosed high-throughput hybridization and reading method for biochips. The high-throughput hybridization and reading system for biochips is suitable for SNP detection of various types, such as bioassay, clinical medicine detection, prediction and diagnosis of catastrophic diseases, plotting of genetic maps, animal and plant inspection and quarantine, and so on.

The high-throughput hybridization and reading system for biochips can simultaneously detects plural SNP loci in a single chip. The system comprises:

an amplification unit, for a) performing PCR amplification on a double-stranded DNA, and marking one of its strands with a marker;

a separation unit, for b) separating the amplified double-stranded DNA, keeping the DNA strand labeled with the marker, and naming it as a to-be-detected DNA strand;

a polymerase chain reaction unit, for c) introducing the to-be-detected DNA strand, a first probe, a second probe, and a third probe into one reaction system for polymerase chain reaction, wherein, the 3'-end through 5'-end of the first probe are a first hybridization region and a first complementary region, respectively, and the 5'-end is an A base or a G base; the 3'-end through 5'-end of the second probe are a second hybridization region and a second complementary region, respectively, and the 5'-end is a C base or a T base; the 5'-end of the third probe is attached to fluorescent groups or chromophoric groups; and: neither of the first and the second hybridization regions is complementary to the to-be-detected DNA, both of the first and the second complementary regions are complementary to the to-be-detected DNA strand, the 5'-end of the second or the first probe is complementary to an SNP locus of the to-be-detected DNA, the first probe and the second probe have at least 10 same bases from their 5'-ends to the 3'-ends and have different intervals, which comprise at least 50% of all bases of each probe; and a chip hybridization detection unit, for d) when the polymerase chain reaction ends, transferring the reaction liquid to the biochip, which has been fixed with fragments complementary to the first hybridization region of the first probe and the second hybridization region of the second probe, respectively, thereby accomplishing hybridization of the single SNP locus;

for detection of multiple SNP loci, depending on SNP loci of the be-detected DNA, designing a first, a second, and a third probe sequences, and repeating Step a) through Step d), so as to obtain a chip or chips having the plural SNP loci; and performing specific reaction with the resulting chip(s) to obtain precipitation or fluorescence, and determining types of the SNP loci according to results of the specific reaction.

According to a preferred mode, the marker in Operation a) includes but is not limited to: a biotin, an avidin, and a streptavidin.

According to a preferred mode, the fluorescent group of the third probe in Operation c) includes but is not limited to: FAM, HEX, TET, JOE, TAMRA, Texas Red, ROX, CY3 and CY5.

According to a preferred mode, the surface of the biochip is fixed with a large number of label-complementary probes corresponding to different single-nucleotide polymorphism loci.

The present invention has one or more of the following beneficial effects:

As compared to the prior art, the disclosed high-throughput hybridization and reading method for biochips uses probes with different marks to specifically connect single nucleotide loci, the probes are connected with target genes at different temperatures, hybridizations are performed at the same temperature after the probes are connected, thereby achieving hybridization detection for various loci in a single chip. The present invention adopts digoxin markers or fluorescent markers to address the problem with the Taqman probes that are highly temperature-dependent, and can only detect a single-nucleotide locus at one time. With the three different probes to match to-be-detected SNP locus, the present invention allows parallel detection of different SNP locus, and can accurately read information of SNP locus from the chips. The detection of samples and SNP locus is sensitive and high-throughput, while significantly reduces detection costs and use of fluorescence probes. Moreover, the detection results are highly repeatable and uniform. The method supports parallel tests and readings in just a few steps, so the operation is simple and convenient. Besides, the chip is easy to prepare and operate, so the method is worthy of promotion.

According to the present invention, a large number of different label-complementary probes are fixed on the surface of biochips, different label complementary probes corresponding to different single-nucleotide polymorphism locus, therefore this method can simultaneously detect more than one hundred different single-nucleotide polymorphism loci.

According to the present invention, the label-complementary probes in the biochip have a relatively high melting point, and hybridization between the label-complementary probe and the label probe is highly specific, so the time required by detection can be significantly decreased.

The present invention provides an open system because the probes in the biochip are label-complementary and independent of the detection objects. By simply changing the probes in the solution hybridization system, detection of different detection objects can be achieved without changing the probes in the biochip. Thus, the biochip of the present invention is applicable to detection of various single-nucleotide polymorphism variations. The present invention is convenient, fast, sensitive, and specific, thus having extensive applications. The present invention can be used to detect trace nucleic-acid samples, can identify genotypes among tens of thousands of highly parallel polymorphism variations, and can be used in identifying pathogenic microorganism, disease diagnosis, locating pathogenic loci, quantitative trait locus analysis, identifying loss of heterozygosity of cancer genes and related researches.

DETAILED DESCRIPTION

The invention as well as a preferred mode of use, further objectives and advantages thereof will be best understood by reference to the following detailed description of illustrative embodiments when read in conjunction with the accompanying drawings.

Unless stated otherwise, the experiment methods used in the following embodiments are all those conventional. Unless stated otherwise, the experiment materials used in the following embodiments are all commercially available.

Embodiment 1

I. Probe Design

In the present invention, different probes correspond to different single-nucleotide loci. The present invention places no particular limitations on the location of different single-nucleotide loci in a genomic DNA. The different probes are designed according to to-be-detected single-nucleotide loci. The present invention places no particular limitations on how the probe is designed, and the design can be done using any probe design principles and software known to people skilled of the art. For example, multiple sequence alignment software such as Clustal may be used to do multiple sequence alignment, and LSPD software may be used to design probes and primers.

Figure 1:
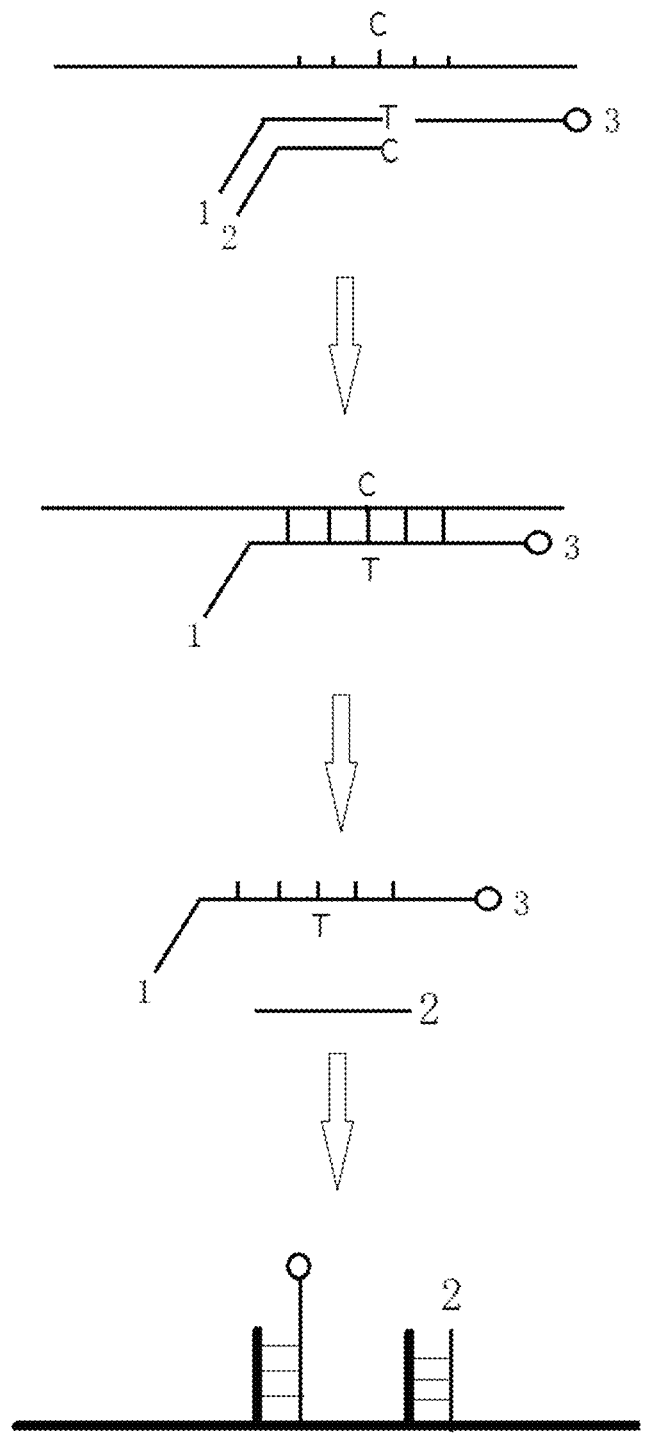
FIG. 1 illustrates the principle of hybridization and reading according to the present invention.

In the present embodiment, the to-be-detected SNP loci are two SNP loci in an APOE gene, located in Locus 112 and Locus 158. The sequence is as described in SEQ ID NO: 1 and is shown below, wherein the to-be-detected SNP loci are bold and underlined:

ggcacggctgtccaaggagctgcaggcggcgcaggcccggctgggcgcg gacatggaggacgtgtgcggccgcctggtgcagtaccgcggcgaggtgc aggccatgctcggccagagcaccgaggagctgcgggtgcgcctcgcctc ccacctgcgcaagctgcgtaagcggctcctccgcgatgccgatgacctg cagaagcgcctggcagtgtaccaggccggggcccgcgagggcgccgagc gcggcctcagcgccatccgcga As shown in FIG. 1, the first probe 1 and the second probe 2 are designed according to SNP loci of the to-be-detected fragment. Therein, the first probe 1 and the second probe 2 each have a length of 30 bp. The first probe 1 has a first hybridization region and a first complementary region from its 3'-end, and its 5'-end is an Abase. The 3'-end through 5'-end of the second probe are a second hybridization region and a second complementary region, respectively, and the 5'-end is a C base. The first probe and the second probe are different in all the 12 bases in their hybridization regions, yet in the complementarity regions, their 17 bases are the same and match the amplified products. This ensures that the first probe and the second probe have at least 10 same bases from their 5'-end to 3'-end and have different intervals, which comprise at least 50% of all bases of each probe. The 5'-end of the third probe is attached to fluorescent groups or chromophoric groups. The complementary region of the second probe and the first probe hybridize with the to-be-detected fragment. The spotting probe is complementary to the hybridization region of the first or the second probe. The third probe and the first probe are complementary to the to-be-detected fragment at two sides of the to-be-detected SNP locus. After match, with the effect of Taq polymerase, a complete probe strand is formed.

According to the foregoing probe design rules, the probes of the present embodiment are as shown in Table 1 below:

TABLE 1

| Locus | Probe | SEQ ID NO. | DNA Sequence (3'-5') |
|---|---|---|---|
| APOE | First Probe 1 | 4 | gcggtagtaccatacggtacctcctgcaca |
| Locus 112 | Second Probe 2 | 5 | acttggtctagccgacctacctcctgcacc |
|  | Spotting Probe 1 | 6 | cgccatcatggtatgcc |
|  | Spotting Probe 2 | 7 | tgccacagatcggctgg |
|  | Chromogenic Probe 5 | 8 | cgccggcggaccacgtcatgg |

TABLE 1-continued

| Locus | Probe | SEQ ID NO. | DNA Sequence (3'-5') |
|---|---|---|---|
| APOE | First Probe 3 | 9 | cgtcatgtgcaatccgactggacgtcttcg |
| Locus 158 | Second Probe 4 | 10 | atggagcattccgaacgctggacgtcttct |
| | Spotting Probe 3 | 11 | gcagtacacgttaggct |
| | Spotting Probe 4 | 12 | tacctcgcggattcgac |
| | Chromogenic Probe 6 | 13 | cggaccgtcacatggtccggc |

In the present embodiment, the probes match the to-be-detected fragment from its 5'-end. In other words, the first probe has from its 3'-end the first hybridization region and the first complementary region successively, and the 5'-end is an A base or G base. The 3'-end through 5'-end of the second probe are the second hybridization region and the second complementary region, respectively, and the 5'-end is a base C or T. The 5'-end of the third probe is connected with fluorescent groups or chromophoric groups. In a different design scheme, the probes match the to-be-detected fragment from its 3'-end instead. In other words, the first probe has from its 5'-end the first hybridization region and the first complementary region successively, and the 3'-end is an A base or a G base. The second probe has from its 5'-end the second hybridization region and the second complementarity region successively, and the 3'-end is a base C or T. The third probe has is 5'-end phosphorylated, and has its 3'-end connected with fluorescent groups or chromophoric groups. This forms a design directionally opposite to the present embodiment, yet similarly achieving match and hybridization.

II. Double-Stranded PCR Amplification

PCR double-stranded amplification is performed on the to-be-detected fragment, and one strand of the amplified product is connected with biotin microspheres to facilitate strand separation.

Primers are designed as below according to the to-be-amplified fragment:

ApoE-primer-1 (as described in SEQ ID NO: 2):
tcgcggatggcgctga

ApoE-primer-2 (as described in SEQ ID NO: 3):
biotin-ggcacggctgtccaagga

Therein, one end of Primer 2 is connected with biotin microspheres.

The PCR amplification system is a 250 µL reaction system, which comprises: 10×PCR buffer solution 2 µL, 25 mM MgCl 1.5 µL, 0.2 mM×dNTPs 0.5 µL, 5 U/µL Taq DNA polymerase 0.25 µL, 100 µM forward primer 0.1 µL, 100 µL, 100 µM reverse primer 0.1 µL, and ddH20 making up to 25 µL. Therein, the 5'-end of the forward primer is connected with biotin label.

The PCR polymerase chain reaction is performed with the following conditions: 95° C. initial denaturation 5 min; 95° C. 2 s; 58° C. 10 s; 60° C. 1 min, 40 cycles in total.

In the present invention, the forward primer and reverse primer are primers designed according to the to-be-detected SNP locus. The present invention places no particular limitations on how the primers are designed, and the design may be done using any primer design method known to people skilled of the art. The present invention places no particular limitations on the conditions of the polymerase chain reaction, and conventional PCR reaction conditions known to people skilled of the art may be used.

III. DNA Strand Separation

DNA strand separation may be realized by filtration separation using a DNA strand separation device, or using other known methods. The DNA strand separation device uses polyethylene microspheres as its membrane filter material, with gaps between the microspheres preferably being 10 µm, smaller than the diameter of the biotin, so that by direct physical filtration, single strands with affinity linker can be kept on the membrane, the strands without the affinity linker are filtered off. The device provides good adsorption and elution, and has a high DNA recovery rate. Besides, the material is inexpensive and environmentally friendly.

The separation process involves: adding 0.4M NaOH and 1M NaCl to unwind the double stranded helix, gently blowing and agitating for homogenization, centrifuging at 12000 rmp for 1 min; washing off residual NaOH, neutralizing to neutrality in pH, centrifuging at 12000 rmp for 1 min; with the to-be-detected fragment retained by the membrane filter, adding a collecting liquid such as ultrapure water, then gently blowing and agitating until the DNA strand fully suspend, collecting the strand, sealing up and storing at 4° C. for later use.

IV. Integrated Reaction for Hybridization and Reading

Hybridization of the first probes 1, 3 and the second probes 2, 4 and the third probes 5, 6 with the single-stranded DNA is performed using a DNA ligase. The hybridization system works with the following conditions: 95° C. 30 s, 60° C. 30 s, 72° C. 30 s, 35 cycles in total. For hybridization, the DNA ligase may be T4 DNA ligase or a thermostable DNA ligase. For better ligation, a thermostable DNA ligase is preferred. The buffer solution used in the hybridization system may be formulated similarly as to that for amplification.

The chromogenic probes are diluted to 5 pmol/µl. The first probe or the second probe has a concentration of 0.25 to 1 pmol/µl. For preparing the hybridization solution, 1 µl of the first probe or the second probe, and 1 µl of the chromogenic probe are added into 250 µl hybridization buffer. The resulting hybridization solution and the amplified products go through hybridization reaction together.

After hybridization, a hybrid "amplified product—first probe 1—third probe 5" and a hybrid "amplified product—first probe 3—third probe 6" are formed. The hybrids are eluted and neutralized to pH7-8 using the eluate for chip hybridization detection.

A spotting probe 1 matching the first probe 1 and a spotting probe 2 matching the second probe 2 are fixed to the chip. The spotting probes are diluted to 10 pmol/ul, and spot on the chip in order.

The sequence of the spotting probe 1 is complementary to the first hybridization region of the first probe 1, and the sequence of the spotting probe 2 is complementary to the second hybridization region of the second probe 2. The first probe 1 and the second probe 2 are hybridized with the sequences fixed to the chip, respectively. After hybridization, the identification fragment at the end of the first probe or the second probe is used to perform SNP locus variant identification. The chip is generally made of a nylon membrane, while a glass sheet or a silicone sheet is also usable After the reaction, the reactant is washed, and a digoxin antibody is added for further reaction. After the further reaction, the reactant is washed again. Then a chromogenic solution is added for chromogenic reaction. Hybridization, antibody reaction, and chromogenic reaction each take 10 minutes.

Since the signal probe exclusively has perfect match with a single genotype of the SNP locus, the type of the bases of the to-be-detected SNP locus can be identified according to chromogenic result of the chip.

After hybridization of the probes and the amplified products, centrifuging is performed to remove unbound parts, and a digoxin antibody is added to react with the digoxin at the end of the hybridized third probe. After the reaction, the antibody is washed off, and catalysis is performed using BCIP/NBT to form blue-violet precipitation on the surface of the chip.

Where the chromogenic probe is terminated with fluorescent groups, the foregoing antibody reaction can be eliminated and fluorescence at different sites in the chip can be directly observed.

Figure 2:
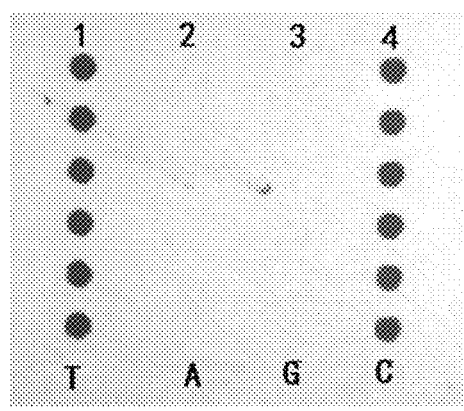
FIG. 2 is a biochip hybridization spectrum of an experiment according to an embodiment of the present invention.

In the present embodiment, at Locus 112, the first probe 1 and the chromogenic probe 3 perfectly match the amplified products. At Locus 158, the first probe 3 and the chromogenic probe 6 perfectly match the amplified products. As shown in FIG. 2, the first column represents the spotting probe 1, the second column represents the spotting probe 2, the third column represents the spotting probe 3, and the fourth column represents the spotting probe 4. During hybridization of chips, only the first probe 1 and the first probe 3 are left in the reaction system to match the spotting probes in the chip. Therefore, the first column and the fourth column form blue-violet precipitation on the surface of the chip. This further shows that the base sequence at Locus 112 is T, and the base sequence at Locus 158 is C.

In the present embodiment, each of the first and second probes is made with three different concentrations (0.25 pmol/µL, 0.5 pmol/µL, and 1 pmol/µL). Each concentration corresponds to two sets of parallel tests, amounting to 6 sets. The results of the parallel tests are shown in FIG. 1. Precipitation is formed at the same probes.

The disclosed hybridization and reading system can accomplish simultaneous parallel analysis of 24 samples in merely 60 minutes. The detection results are consistent and the operation is convenient yet effective. The precipitation results are captured using external cameras and the images are automatically processed so that the signal points showing after hybridization chromogenic reaction are marked. After hybridization, the chromogenic location of reaction sites in the chip or the chromogenic intensity can be analyzed using a chip scanner and related software, and the imaging signals can be converted into data to provide the related biological information, thereby rapidly completing the entire operation from the raw samples to the desired analysis results in a closed system in a short period of time.

More conditions and parameters for the disclosed hybridization and reading process claimed herein can be seen from the existing methods and systems for SNP detection using biochips. The present embodiment is focused on the characteristics of the disclosed method and the difference between the present invention and prior art, and omits unnecessary details that are known to people skilled in the art.

Embodiment 2

The present embodiment is similar to Embodiment 1 with the only difference that fluorescence is used for chip reading. The results are consistent with Embodiment 1.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A high-throughput hybridization and reading method for biochips, which simultaneously detects plural SNP loci in a single chip, for detection of each SNP locus the method comprising the following steps:
   a) performing PCR amplification on a double-stranded DNA to be detected, and marking one of its strands with a marker;
   b) separating the amplified double-stranded DNA, keeping the DNA strand labeled with the marker;
   c) introducing the separated amplified to-be-detected DNA strand, a first probe, a second probe, and a third probe into one reaction system for polymerase chain reaction, wherein,
   the 3'-end through 5'-end of the first probe are a first hybridization region and a first complementary region, respectively, and the 5'-end is an Abase or a G base;
   the 3'-end through 5'-end of the second probe are a second hybridization region and a second complementary region, respectively, and the 5'-end is a C base or a T base; and
   the 5'-end of the third probe is attached to fluorescent groups or chromophoric groups; and:
   neither of the first and the second hybridization regions is complementary to the to-be-detected DNA,
   both of the first and the second complementary regions are complementary to the separated amplified to-be-detected DNA strand,
   the 5'-end of the second probe or the first probe is complementary to an SNP locus of the to-be-detected DNA, the first probe and the second probe have at least 10 same bases from their 5'-ends to the 3'-ends and have different intervals, which comprise at least 50% of all bases of each probe;

d) when the polymerase chain reaction ends, transferring the reaction liquid to the single biochip, which has been fixed with fragments complementary to the first hybridization region of the first probe and the second hybridization region of the second probe, respectively, thereby accomplishing hybridization of the single SNP locus;

designing a first, a second, and a third probe sequences as a function of SNP loci of the separated amplified be-detected DNA, and repeating Step a) through Step d), so as to obtain the single chip for detecting the plural SNP loci; and performing specific reaction with the resulting single chip to obtain precipitation or fluorescence, and determining types of the SNP loci according to results of the specific reaction.

2. The method of claim 1, wherein the marker in Step a) includes but is not limited to: a biotin, an avidin or a streptavidin.

3. The method of claim 1, wherein the fluorescent group of the third probe in Step c) includes but is not limited to: FAM, HEX, TET, JOE, TAMRA, Texas Red, ROX, CY3 and/or CY5.

4. The method of claim 1, wherein the chromophoric group of the third probe in Step c) includes but is not limited to: ECL, NBT/BCIP or DAB.

5. The method of claim 1, wherein the number of the bases in each of the first and second hybridization regions is 15 to 25.

6. The method of claim 1, wherein the number of the bases in each of the first and second complementary regions is 15 to 25.

7. The method of claim 1, wherein detection channels for the fluorescent groups are:
FAM: 465 to 510 nm; CY3: 533 to 580 nm; HEX: 533 to 580 nm; TET:533 to 580 nm; JOE: 533 to 580 nm; Texas Red: 533 to 610 nm; ROX: 533 to 610 nm; CY5: 618 to 660 nm; and TAMRA:533 to 580 nm.

8. The method of claim 1, wherein Tm values corresponding to the probes are independently greater than 25° C.

9. The method of claim 1, wherein the PCR amplification system is a 25 μL reaction system, which comprises: 10×PCR buffer solution 2 μL, 25 mM MgCl 1.5 μL, 0.2 mM×dNTPs 0.5 μL, 5 U/μLTaq DNA polymerase 0.25 μL, 100 μM forward primer 0.1 μL, 100 μM reverse primer 0.1 μL, ddH20 making up to 25 μL.

10. The method of claim 1, wherein the reaction condition for the PCR polymerase chain reaction is: 95° C. initial denaturation 5 min; 95° C. 2 s; 58° C. 10 s; 60° C. 1 min, 40 cycles in total.

* * * * *

SEQUENCE LISTING

<160> NUMBER OF SEQ ID NOS: 13

<210> SEQ ID NO 1
<211> LENGTH: 267
<212> TYPE: DNA
<213> ORGANISM: Artificial Sequence
<220> FEATURE:
<223> OTHER INFORMATION: A synthetic ApoE gene sequence

<400> SEQUENCE: 1

```
ggcacggctg tccaaggagc tgcaggcggc gcaggcccgg ctgggcgcgg acatggagga      60
cgtgtgcggc cgcctggtgc agtaccgcgg cgaggtgcag gccatgctcg gccagagcac     120
cgaggagctg cgggtgcgcc tcgcctccca cctgcgcaag ctgcgtaagc ggctcctccg     180
cgatgccgat gacctgcaga agcgcctggc agtgtaccag gccggggccc gcgagggcgc     240
cgagcgcggc ctcagcgcca tccgcga                                         267
```

<210> SEQ ID NO 2
<211> LENGTH: 16
<212> TYPE: DNA
<213> ORGANISM: Artificial Sequence
<220> FEATURE:

<223> OTHER INFORMATION: A synthetic ApoE primer 1

<400> SEQUENCE: 2
tcgcggatgg cgctga                                                    16

<210> SEQ ID NO 3
<211> LENGTH: 18
<212> TYPE: DNA
<213> ORGANISM: Artificial Sequence
<220> FEATURE:
<223> OTHER INFORMATION: A synthetic ApoE primer 2

<400> SEQUENCE: 3
ggcacggctg tccaagga                                                  18

<210> SEQ ID NO 4
<211> LENGTH: 30
<212> TYPE: DNA
<213> ORGANISM: Artificial Sequence
<220> FEATURE:
<223> OTHER INFORMATION: A synthetic first probe 1

<400> SEQUENCE: 4
gcggtagtac catacggtac ctcctgcaca                                     30

<210> SEQ ID NO 5
<211> LENGTH: 30
<212> TYPE: DNA
<213> ORGANISM: Artificial Sequence
<220> FEATURE:
<223> OTHER INFORMATION: A synthetic second probe 2

<400> SEQUENCE: 5
acttggtcta gccgacctac ctcctgcacc                                     30

<210> SEQ ID NO 6
<211> LENGTH: 17
<212> TYPE: DNA
<213> ORGANISM: Artificial Sequence
<220> FEATURE:
<223> OTHER INFORMATION: A synthetic spotting probe 1

<400> SEQUENCE: 6
cgccatcatg gtatgcc                                                   17

<210> SEQ ID NO 7
<211> LENGTH: 17
<212> TYPE: DNA
<213> ORGANISM: Artificial Sequence
<220> FEATURE:
<223> OTHER INFORMATION: A synthetic spotting probe 2

<400> SEQUENCE: 7
tgccacagat cggctgg                                                   17

<210> SEQ ID NO 8
<211> LENGTH: 21
<212> TYPE: DNA
<213> ORGANISM: Artificial Sequence
<220> FEATURE:
<223> OTHER INFORMATION: A synthetic chromogenic probe 5

<400> SEQUENCE: 8
cgccggcgga ccacgtcatg g                                              21

```
<210> SEQ ID NO 9
<211> LENGTH: 30
<212> TYPE: DNA
<213> ORGANISM: Artificial Sequence
<220> FEATURE:
<223> OTHER INFORMATION: A synthetic first probe 3

<400> SEQUENCE: 9
cgtcatgtgc aatccgactg gacgtcttcg                                          30

<210> SEQ ID NO 10
<211> LENGTH: 30
<212> TYPE: DNA
<213> ORGANISM: Artificial Sequence
<220> FEATURE:
<223> OTHER INFORMATION: A synthetic second probe 4

<400> SEQUENCE: 10
atggagcatt ccgaacgctg gacgtcttct                                          30

<210> SEQ ID NO 11
<211> LENGTH: 17
<212> TYPE: DNA
<213> ORGANISM: Artificial Sequence
<220> FEATURE:
<223> OTHER INFORMATION: A synthetic spotting probe 3

<400> SEQUENCE: 11
gcagtacacg ttaggct                                                        17

<210> SEQ ID NO 12
<211> LENGTH: 17
<212> TYPE: DNA
<213> ORGANISM: Artificial Sequence
<220> FEATURE:
<223> OTHER INFORMATION: A synthetic spotting probe 4

<400> SEQUENCE: 12
tacctcgcgg attcgac                                                        17

<210> SEQ ID NO 13
<211> LENGTH: 21
<212> TYPE: DNA
<213> ORGANISM: Artificial Sequence
<220> FEATURE:
<223> OTHER INFORMATION: A synthetic chromogenic probe 6

<400> SEQUENCE: 13
cggaccgtca catggtccgg c                                                   21
```